United States Patent [19]

Itoga et al.

[11] Patent Number: 5,731,201

[45] Date of Patent: Mar. 24, 1998

[54] METHOD FOR PRODUCING VIRUS-FREE ROOTSTICKS OF HOP

[75] Inventors: Yutaka Itoga; Narushi Suda, both of Sorachi-gun, Japan

[73] Assignee: Sapparo Breweries Limited, Tokyo, Japan

[21] Appl. No.: 499,344

[22] Filed: Jul. 6, 1995

[30] Foreign Application Priority Data

Jul. 28, 1994 [JP] Japan ................................. 6-194621

[51] Int. Cl.$^6$ ................................. C12N 5/00; C12N 5/02
[52] U.S. Cl. .......................... 435/410; 435/420; 435/430; 435/431
[58] Field of Search .................................. 435/410, 420, 435/430, 431

[56] References Cited

PUBLICATIONS

Proceedings Int. Workshop on Hop Virus Diseases Rauis-chholzhausen 1988, pp. 131–134, 1989, H. TN. Kremheller, et al., "Production and Propagation of Virus–Free Hops in Bavaria, Federal Republic of Germany".

Proceedings Int. Workshop on Hop Virus Diseases Rauis-chholzhausen 1988, pp. 123–126, 1989, G. Legrand, et al., "Health Improvement of the Hop Grown in Belgium and Use of Virus–Free Material".

*Primary Examiner*—Leon B. Lankford, Jr.
*Attorney, Agent, or Firm*—Oblon, Spivak, McClelland, Maier & Neustadt, P.C.

[57] ABSTRACT

Disclosed is a method for producing virus-free, rootstocks of hop, which comprises growing a cultured virus-free hop strain in a rooting medium thereby to make it shoot out roots therein followed by culture it in a rootstocks of hop-producing medium having a high saccharide concentration thereby to form rootstocks of hop in the medium. The virus-free, rootstocks of hop are produced under aseptic conditions and are out of the danger of their contamination with viruses, pathogenic vermian or parasites. The plants are highly safe and can be stored well. When planted, these actively shoot out roots and sprouts.

7 Claims, No Drawings

METHOD FOR PRODUCING VIRUS-FREE ROOTSTICKS OF HOP

BACKGROUND OF THE INVENTION

1. Field of the Invention

The present invention relates to a method for producing virus-free rootstocks of a hop (*Humulus lupulus* L.), which can be stored stably and, when planted, actively shoots out roots and sprouts.

2. Background Information

There is known no report referring to the success in the production of vegetative tissue with dormant buds of a hop (hereinafter referred to as a "rootstocks of hop") by cultivation.

Heretofore, the vegetative propagation of clones of a hop has been conducted according to the following methods:

1. Method of using rootstocks of hop:

The essential subterranean stems of a hop with dormant buds are cut out in autumn, stored and then planted in a nursery field or a plant-cultivating field. Since the rootstock is a vegetative tissue having dormant buds, it can be stored and is characterized in that it actively shoots out roots and grows well after planted.

2. Method of planting hop cuttings:

The budding stems, the essential overground stems or the branches of a hop are cut out, the cuttings with at least one node or more are planted to make them shoot out roots, then the thus-rooted cuttings are grown in a nursery field for one year, and the one-year plants thus grown are transplanted in a plant-cultivating field.

3. Method of tissue culture:

Shoot apices of a hop are cultivated by virus-free technology, and the cultured virus-free strains are further cultured and propagated in vitro. The thus-propagated strains are then transplanted in pots and a nursery field and thereafter in a plant-cultivating field in the same manner as in the above-mentioned method of planting hop cuttings.

There are many reports that refer to the danger of contamination of hop plants with various viruses during cultivating them. In the vegetative propagation of a hop according to the method of using rootstocks or the method of planting hop cuttings, the viruses with which the original hop plant has been contaminated are forced onto the propagated hop plants. Such viruses that have heretofore been known in Japan include apple mosaic virus (ApMV), hop latent virus (HLV), hop mosaic virus (HMV), prunus necrotic ring spot virus (PNRV), etc.

When the virus-free hop strains that were obtained by stem apex culture are once taken out of the test tube used and then planted in pots or in a field, there is a great probability that the thus-grown plants are contaminated with viruses via vectors such as aphids, nematodes, etc. or via the sap of the hop seedlings that is dropped when the plants are trimmed. Therefore, in order to protect the cultivated virus-free hop strains from being contaminated with viruses, much labor is needed for providing an exclusively isolated virus-free field, for drastically exterminating and controling vectors and for frequently conducting the necessary test to confirm the absence of viruses in the strains while removing those, if any, contaminated with viruses at an early stage.

When hop plants are internationally transported for introducing new varieties and for experimental cultivation of them, these are required to be quarantined in order to prevent hop plants contaminated with harmful uermian, etc. from being imported. Recently, many countries have imposed their own legal controls on the importation of hop plants by which the hop plants to be imported shall be verified to be free from viruses of the determined kinds.

The inspection of viruses, if any, in hop plants is conducted by an ELISA method. However, hop plants just after having been contaminated with viruses often have only a low viral concentration so that the viral inspection of the plants gives a negative result. For this reason, it is often difficult to verify the fact that the hop plants that were obtained by the conventional methods of using rootstocks of hop or planting hop cuttings are substantially free from viruses.

In theory, this problem can be solved by using cultured virus-free plants in test tube that were obtained by stem apex culture. However, the use of such cultured virus-free hop plants involves other problems. One problem is that particular devices are needed when the plants that were internationally transported and the grown small plants are planted in pots or in a plant-cultivating field. Another problem is that much stress is imparted to the cultured virus-free hop plants during the international transportation needing a long period of time with the result that the small plants grown from the cultured plants cannot actively grow in pots or in a plant-cultivating field.

SUMMARY OF THE INVENTION

An object of the present invention is to eliminate the danger of the contamination of cultured virus-free hop strains with viruses and to provide virus-free, rootstocks of hop which can be stored stably and, when planted, actively grows and shoots out roots and sprouts, by which the above-mentioned problems with cultivated virus-free hop strains are removed.

We, the present inventors have studied the breeding and culture of hop plants for many years while investigating the phenomenon of in-vitro production of rootstocks of hop especially in terms of the conditions for the growth of the rootstocks of hop and, as a result, have found that virus-free, rootstocks of hop not having the above-mentioned problems can be produced by making a cultured virus-free hop strain sufficiently shoot out roots in a root-shooting medium followed by culture it in a medium for producing rootstocks of hop (hereinafter referred to as a "rootstocks of hop-producing medium") having a high saccharide concentration. On the basis of these findings, we have completed the present invention.

Specifically, the present invention provides a method for producing virus-free, rootstocks of hop, which comprises growing a cultured virus-free hop strain in a root-shooting medium thereby to make it shoot out roots therein followed by cultured it in a rootstocks of hop-producing medium having a high saccharide concentration thereby to form rootstocks of hop in the medium. As the first embodiment of the method of the invention, the rootstocks of hop-producing medium contains one or more saccharides selected from glucose, fructose and sucrose. As the second embodiment of the method of the invention, the rootstocks of hop-producing medium having a high saccharide concentration contains monosaccharide(s) at a concentration of from 0.15 to 1M. As the third embodiment of the method of the invention, the rootstocks of hop-producing medium having a high saccharide concentration contains disaccharide(s) at a concentration of from 0.1 to 0.5M. As the fourth embodiment of the method of the invention, the rootstocks of hop-producing medium having a high saccharide concentration contains glucose at a concentration of from 0.15 to 1M. As the fifth embodiment of the method of the invention, the rootstocks of hop-producing medium having a high saccharide concentration comprises a basic MS medium to which has been added glucose at a concentration of from 0.15 to 1M. As the sixth embodiment of the method of the invention, the cultured virus-free hop strain is obtained by meristem culture.

DETAILED DESCRIPTION OF THE INVENTION

The cultured virus-free hop strain to be used in the present invention can be obtained by cultivating hop plants, even though having been contaminated with viruses, at about 35° C. for 10 to 18 days, then collecting the tips of the stems of from 1 to 5 cm and cultivating them. However, as a more simple and more accurate method for obtaining the strain, the growing point tissue is collected from the tips of shoots of hop and this is cultured by meristem culture to obtain the intended, cultured virus-free hop strain.

To confirm the absence of viruses in the hop strain thus obtained, the strain is subjected to vital inspection according to an ELISA method such as that mentioned hereinabove.

Terminal buds and axillary buds of a plant always have shoot apex meristematic tissue, which is referred to as a growing point or shoot apex tissue. The cultivation of the growing point or shoot apex tissue is referred to as meristem culture.

The shoot apex tissue generally exists in the innermost part of buds and is mostly wrapped with leaves or ramenta to be therefore free from germs. In addition, it is said that almost no virus exists in this tissue at the part of 0.3 mm from its tip. Therefore, it is possible to produce a virus-free hop tissue by cutting out and cultivating the part of this tissue. According to such meristem culture, not only viruses can be removed from the cultivated tissue but also it is possible to obtain an axenic tissue having neither fungi nor bacteria therein.

One concrete method of meristem culture is mentioned. A part of a hop tissue containing terminal buds or axillary buds is cut out in a suitable size and collected. Afterwards, the tissues of ramenta and leaves covering the shoot apex tissue are removed to make the shoot apex tissue exposed by using a stereoscopic microscope in a clean bench, then the thus-exposed shoot apex tissue is cut with a sterile sharp cutter such as a surgical knife or the like into pieces having a thickness of from 0.15 mm to 0.3 mm, and these pieces are collected.

These pieces are collected while they are on the tip of the cutter, and these are immediately put onto a medium. The medium may be an ordinary one that is generally used for plant tissue culture, including, for example, Murashige-Skoog (hereinafter referred to as MS) medium, White medium, Linsmaier-Skoog medium, Nitsch medium, etc. Popularly used is an MS agar medium to which have been added vegetable hormones such as auxin, cytokinin, etc. As one preferred example, mentioned is a medium comprising a basic MS medium to which have been added 2.0 mg/liter of benzyladenine (BA), 0.2 mg/liter of gibberellic acid ($GA_3$) and 20 g/liter of glucose (pH 5.8; agar content 8 g/liter).

The culture of the shoot apex tissue thus put onto the medium is conducted at room temperature for about one month, whereupon one shoot apex tissue grows to be able to be divided into about 10 clones (that is, the tissue grows to be a cultured strain having about 10 terminal buds or lateral buds). After cultivated for one month more, the divided clones further propagate to yield about 10 clones each. The propagation culture may be conducted in accordance with the necessary number of the clones. For example, if 1000 clones are necessary, the shoot apex tissue put onto the medium shall be cultivated for about 3 months; and if 10000 clones are necessary, the same shall be cultivated for about 4 months.

The thus-obtained tissues are subjected to viral inspection according to an ELISA method, by which they are confirmed to be free from viruses.

The clones propagated are further cultured and grown for one month more and thereafter subjected to growing culture.

Next, the virus-free tissues are subjected to growing culture by which the growth of the apical dominant phase is promoted. Namely, the precocial branching phase in the cultured strain is efficiently converted into the apical dominant phase. For this culture, preferably used is the above-mentioned MS agar medium to which have been added 0.2 mg/liter of indole-acetic acid and 20 g/liter of glucose (pH 5.8; agar content 8 g/liter).

This culture is conducted at room temperature for about 2 months. After the conversion into the apical dominant phase in the thus-cultured tissue has been confirmed, the tissue is then subjected to rooting culture.

The rooting culture is conducted, using an MS agar medium to which have been added 0.2 mg/liter of indole-butyric acid and 20 g/liter of glucose (pH 5.8; agar content 8 g/liter). Concretely, the cultured tissue is put onto the medium and again cultured thereon at room temperature for from 2 weeks to about one month, thereby making the tissue sufficiently shoot out roots.

The thus-cultured virus-free hop strain (that has shot out roots) is further cultured in a rootstocks of hop-producing medium to obtain virus-free, rootstocks of hop.

As the basic medium of the rootstocks of hop-producing medium, used is any one of the above-mentioned ordinary vegetable tissue-cultivating liquid media such as liquid MS medium. The rootstocks of hop-producing medium for use in the present invention contains saccharide(s) at a high concentration. Concretely, it contains one or more saccharides selected from glucose, fructose, sucrose, etc. The saccharide concentration in the medium may be from 0.15 to 1M, preferably from 0.2 to 0.4M, for monosaccharides such as glucose, fructose, etc.; while it may be from 0.1 to 0.5M, preferably from 0.1 to 0.2M, for disaccharides such as sucrose, etc. If the saccharide concentration is lower than the defined range, the producibility of the intended rootstocks of hop in the medium is noticeably lowered even though the strain being cultured may still live therein. On the contrary, if it is higher than the defined range, the growth of the strain being cultured is retarded or the strain will die.

One preferred example of the medium comprises liquid MS medium containing from 0 to 2.0 mg/liter, preferably from 0.1 to 0.2 mg/liter of indole-butyric acid and from 30 to 150 g/liter, preferably from 40 to 60 g/liter of glucose, which has pH of 5.8.

The medium may have pH of from 5.5 to 6.0, preferably from 5.7 to 5.8.

The culture is conducted in a test tube, which may have a size of approximately from 10×80 mm to 30×200 mm, preferably approximately from 15×90 mm to 25×120 mm. This is because sufficient growth of the cultured hop strain is impossible in test tubes smaller than the defined range and the strain that has grown insufficiently produces only small-sized rootstocks of hop even though planted. On the other hand, the producibility of the intended rootstocks of hop is poor if the cultured hop strain is grown in test tubes larger than the defined range.

According to the present invention, the cultured virus-free hop strains are transplanted on the medium in a test tube and are further cultured thereon at from 20° to 30° C., preferably at 25° C., always in light at from 3,000 to 25,000 luxes, preferably from 15,000 to 20,000 luxes, or are further cultivated thereon at from 20° to 30° C., preferably at 25° C., in light at from 3,000 to 25,000 luxes for the first 14 to 20 hours and then at from 10° to 20° C., preferably at 15° C., in the absence of light for the next 4 to 10 hours. Under these conditions, the strains are cultured for from 1 to 3 months while repeating the cycle in the latter case. The cultured virus-free hop strains shall be transplanted on the medium after the rooting medium is completely removed from the strains.

After thus cultured for about 1 month, the strains begin to grow in thickness at any site above their main stem base. After about 2 months, almost all the strains cultured produce rootstocks. At this stage, the tip stems and the leaves of the cultured strains begin to be blighted, while the thus-produced rootstocks further grow in thickness. After about 3 months, no significant increase in the producibility of the dormant seedlings is admitted and the culture is finished.

From 70 to 100% of the strains thus cultivated according to the cultivation process mentioned above produce thickened rootstocks at any site above the main stem bases.

The present invention is described in more detail by means of the following examples, which, however, are not intended to restrict the scope of the present invention.

EXAMPLE 1

The meristem (growing point tissue) at the tips of the stems of a hop were collected at a thickness of 0.2 mm and put onto a medium comprising a basic MS medium that had been put in a test tube of 17×105 mm size. The medium had a composition comprised of 370 mg/liter of $MgSO_4.7H_2O$, 440 mg/liter of $CaCl_2.2H_2O$, 1900 mg/liter of $KNO_3$, 1650 mg/liter of $NH_4NO_3$, 170 mg/liter of $KH_2PO_4$, 27.8 mg/liter of $FeSO_4.7H_2O$, 37.3 mg/liter of $Na_2$-EDTA, 22.3 mg/liter of $MnSO_4.4H_2O$, 8.6 mg/liter of $ZnSO_4.7H_2O$, 0.025 mg/liter of $CuSO_4.5H_2O$, 0.025 mg/liter of $CoCl_2.6H_2O$, 0.83 mg/liter of KI, 6.2 mg/liter of $H_3BO_3$, 0.25 mg/liter of $Na_2MoO_4.2H_2O$, 100 mg/liter of myoinositol, 0.5 mg/liter of nicotinic acid, 0.5 mg/liter of pyridoxine hydrochloride, from 0.1 to 1 mg/liter of thismine hydrochloride and 2 mg/liter of glycine, to which were added 2.0 mg/liter of benzyladenine, 0.2 mg/liter of gibberellic acid and 20 g/liter of glucose. This had a pH of 5.8 and an agar content of 8 g/liter. On this medium, these shoot spices were cultured by stem apex culture under cycle conditions for about 3 months. One culture cycle was such that the apices were cultured at 25° C. in light for 16 hours (at from 5,000 to 20,000 luxes) and then in the absence of light for 8 hours. During the cultivation, the cultured strains were confirmed to be free from viruses by an ELISA method. The thus-cultured virus-free hop strains were divided, transplanted and sub-cultured two times thereby reproducing 100 virus-free hop clones. These were again cultured for one month more to be grown further.

Next, these 100 virus-free hop clones were put onto a medium comprising the above-mentioned basic MS medium, to which had been added 0.2 mg/liter of indole-acetic acid and 20 g/liter of glucose. This medium had a pH of 5.8 and an agar content of 8 g/liter. These were cultured thereon at room temperature for about 2 months whereby the growth of the apical dominant phase in these was promoted.

The thus-cultured 100 clones were put onto a medium comprising the basic MS medium, to which had been added 0.2 mg/liter of indole-butyric acid and 20 g/liter of glucose. This medium had a pH of 5.8 and an agar content of 8 g/liter. These clones were further cultivated on the medium at room temperature for from 2 weeks to about one month thereby making them sufficiently shoot out roots.

Next, the medium adhered to the roots and the other parts of the thus-rooted virus-free hop clones were carefully removed under aseptic conditions. These 100 clones were used for producing virus-free, rootstocks of hop in the next step. Concretely, the virus-free clones were transplanted in test tubes (17×105 mm size) each containing 4 ml of a liquid medium (pH 5.8) comprising the basic MS medium, to which had been added 0.2 mg/liter of indole-acetic acid and 40 g/liter of glucose, and cultivated therein under cycle conditions. One culture cycle was such that the clones were cultured at 25° C. in light for 16 hours (at from 5,000 to 20,000 luxes) and then at 15° C. in the absence of light for 8 hours.

After thus cultured for about 1 month, the clones began to grow in thickness at any site above their main stem bases. After about 2 months, 82 of these 100 clones (82%) were found to have produced rootstocks. At this stage, the tip stems and the leaves of the cultured clones began to be blighted, while the produced rootstocks further grew in thickness. After about 3 months, any significant increase in the producibility of the rootstocks was no more admitted and the cultivation was finished. The thus-produced rootstocks were collected. The fresh weight of the rootstocks produced was 0.26 g on average (the smallest one weighed 0.14 and the largest one weighed 0.42 g).

EXAMPLE 2

The same process as in Example 1 was repeated, except that the stem apex culture was conducted in test tubes of 25×120 mm size and that the rootstocks of hop-producing culture was also in test tubes of 25×120 mm size. As a result, 79% of the cultured clones produced rootstocks of hop in 3 months, and the fresh weight of the rootstocks of hop produced was 0.51 g on average.

EXAMPLE 3

The same process as in Example 1 was repeated, except that the stem apex culture was conducted in test tubes of 30×200 mm size and that the rootstocks of hop-producing culture was also in test tubes of 30×200 mm size. As a result, 26.7% of the cultured clones produced rootstocks of hop in 3 months, and the fresh weight of the rootstocks of hop thus produced was 0.79 g on average.

The present invention has been described in detail hereinabove, especially with referring to the preferred embodiments thereof. There is a probability that the virus-free, rootstocks of hop to be collected in a farming field will be again contaminated with viruses via vectors or during farming them. However, the virus-free, rootstocks of hop to be produced under aseptic conditions according to the present invention are out of the danger of their contamination with viruses, pathogenic vermian or parasites and are therefore highly safe. In addition, these can be stored well and, when planted, these actively shoot out roots and sprouts.

While the invention has been described in detail and with reference to specific embodiments thereof, it will be apparent to one skilled in the art that various changes and modifications can be made therein without departing from the spirit and scope thereof.

What is claimed is:

1. A method for producing virus-free rootstocks of hop, which comprises growing a cultured virus-free hop strain in a rooting medium thereby to make it shoot out roots in the medium followed by cultivating it in a rootstocks of hop-producing medium having a high saccharide concentration thereby to form rootstocks of hop in the medium.

2. The method as claimed in claim 1, in which the saccharide of the rootstocks of hop-producing medium is one or more saccharides selected from glucose, fructose and sucrose.

3. The method as claimed in claim 1, in which the rootstocks of hop-producing medium contains monosaccharide at a concentration of from 0.15 to 1M.

4. The method as claimed in claim 1, in which the rootstocks of hop-producing medium contains disaccharide at a concentration of from 0.1 to 1M.

5. The method as claimed in claim 1, in which the rootstocks of hop-producing medium contains glucose at a concentration of from 0.15 to 1M.

6. The method as claimed in claim 1, in which the rootstocks of hop-producing medium comprises a basic MS medium to which glucose is added at a concentration of from 0.15 to 1M.

7. The method as claimed in claim 1, in which the cultured virus-free hop strain is a strain obtained by stem apex culture.

* * * * *

UNITED STATES PATENT AND TRADEMARK OFFICE
CERTIFICATE OF CORRECTION

PATENT NO. : 5,731,201
DATED : March 24, 1998
INVENTOR(S) : Yutaka ITOGA, et al.

It is certified that error appears in the above-identified patent and that said Letters Patent is hereby corrected as shown below:

On the title page, item [73] should be:

--[73] Assignee: Sapporo Breweries Limited, Tokyo, Japan--

Signed and Sealed this

Nineteenth Day of May, 1998

*Attest:*

BRUCE LEHMAN

*Attesting Officer*     *Commissioner of Patents and Trademarks*